United States Patent
Huang et al.

(10) Patent No.: US 11,576,930 B2
(45) Date of Patent: Feb. 14, 2023

(54) METHODS AND COMPOSITIONS FOR TREATMENT OF MULTI-DRUG RESISTANT TUMORS

(71) Applicant: SUN YAT-SEN UNIVERSITY, Guangdong (CN)

(72) Inventors: Yijun Huang, Guangdong (CN); Danyang Liu, Guangdong (CN); Juncheng Pan, Guangdong (CN); Yang Hu, Guangdong (CN); Zhu Zhu, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 119 days.

(21) Appl. No.: 16/637,142

(22) PCT Filed: Aug. 8, 2017

(86) PCT No.: PCT/CN2017/096331
§ 371 (c)(1),
(2) Date: Feb. 6, 2020

(87) PCT Pub. No.: WO2019/028646
PCT Pub. Date: Feb. 14, 2019

(65) Prior Publication Data
US 2020/0368274 A1 Nov. 26, 2020

(51) Int. Cl.
| | |
|---|---|
| *A61K 33/243* | (2019.01) |
| *A61P 35/00* | (2006.01) |
| *A61K 31/136* | (2006.01) |
| *A61K 31/4709* | (2006.01) |
| *A61K 31/7052* | (2006.01) |
| *A61K 31/708* | (2006.01) |

(52) U.S. Cl.
CPC .......... *A61K 33/243* (2019.01); *A61K 31/136* (2013.01); *A61K 31/4709* (2013.01); *A61K 31/708* (2013.01); *A61K 31/7052* (2013.01); *A61P 35/00* (2018.01)

(58) Field of Classification Search
CPC .................................................. A61K 33/243
See application file for complete search history.

(56) References Cited

FOREIGN PATENT DOCUMENTS

| | | | |
|---|---|---|---|
| CN | 1520886 A | * | 8/2004 |
| CN | 104328122 A | | 2/2015 |
| CN | 106632323 A | | 5/2017 |
| WO | WO-97/33575 A1 | | 9/1997 |

(Continued)

OTHER PUBLICATIONS

Holohan et al, Nature Reviews Cancer vol. 13, pp. 714-726 (2013). (Year: 2013).*

(Continued)

*Primary Examiner* — Benjamin J Packard
(74) *Attorney, Agent, or Firm* — Foley & Lardner LLP

(57) ABSTRACT

Methods for treatment of a multi-drug resistant (MDR) tumor in a subject are disclosed. The methods comprise administering to the subject in need of treatment a therapeutically effective amount of an anti-*mycoplasma* agent and/or an agent blocking the interaction between membrane protein P37 of *mycoplasma* and Annexin A2 of host cells of the subject, prior to, at the same time with, or after chemotherapy. Relevant pharmaceutical compositions, kits, uses are also disclosed.

5 Claims, 12 Drawing Sheets

(56) References Cited

FOREIGN PATENT DOCUMENTS

| WO | WO-2009/138507 A2 | 11/2009 |
|---|---|---|
| WO | WO-2012/117246 A1 | 9/2012 |

OTHER PUBLICATIONS

Yuan et al (2016) N-Terminal Polypeptide of Annexin A2 Decreases Infection of Mycoplasma hyorhinis to Gastric Cancer Cells. PLOS ONE 11(1): e0147776. https://doi.org/10.1371/journal.pone.0147776). (Year: 2016).*

Liekens et al., "Improvement of purine and pyrimidine antimetabolite-based anticancer treatment by selective suppression of mycoplasma-encoded catabolic enzymes", 2009, vol. 30, pp. 628-635 (9 pages).

Liu et al., "Mycoplasma-associated multidrug resistance of hepatocarcinoma cells requires the interaction of P37 and Annexin A2", PLOS, 2017, pp. 1-14 (15 pages).

Sassa et al., "Therapeutic Effect of Claithromycin on a Transplanted Tumor in Rats", Antimicrobial Agents and Chemotherapy, 1999, Vo. 43, No. 1, pp. 67-72 (6 pages).

Shcheblyakov et al., "Mycoplasma Infection with M. Arginini Results in NF-kB Constitutive Activation and Inhibition of Apoptosis in Cells Expressing Toll-Like Receptors TLR2/6", Molecular Genetics, Microbiology and Virology, 2009, vol. 23, No. 4, pp. 163-167 (5 pages).

Voorde et al., "Nucleoside-Catabolizing Enzymes in Mycoplasma-Infected Tumor Cell Cultures Compromise the Cytostatic Activity of the Anticancer Drug Gemcitabine", The Journal of Biological Chemistry, 2014, pp. 1-24 (25 pages).

Wang et al., "Reversal Effect of BM-cyclin 1 on Multidrug Resistance by Down-regulating MRP2 in BALB/C Nude Mice Bearing C-A120 Cells", J. Huazhong Univ. Sci. Technol., 2013, vol. 33, No. 6, pp. 840-844 (5 pages).

Yuan et al., "N-Terminal Polypeptide of Annexin A2 Decreases Infection of Mycoplasma hyorhinis to Gastric Cancer Cells", PLOS ONE, 2016, pp. 1-16 (16 pages).

Zhang et al., "The Association of Annexin A2 and Cancers", Clin. Transl. Oncol., 2012, vol. 14, pp. 634-640 (7 pages).

International Search Report and Written Opinion issued in PCT Application No. PCT/CN2017/096331 dated May 9, 2018, 9 pages.

Fang, et al., "Reversal effect on human lung adenocarcinoma multidrug resistance cell line A549/ADM by azithromycin," Acta Universita Medicina 41(2):172 (2006) English abstract only.

Zhang, et al., "Annexin A2 is implicated in multi-drug-resistance in gastric cancer through p38MAPK and AKT pathway," Neoplasma 61(6):627-637 (2014).

\* cited by examiner

B
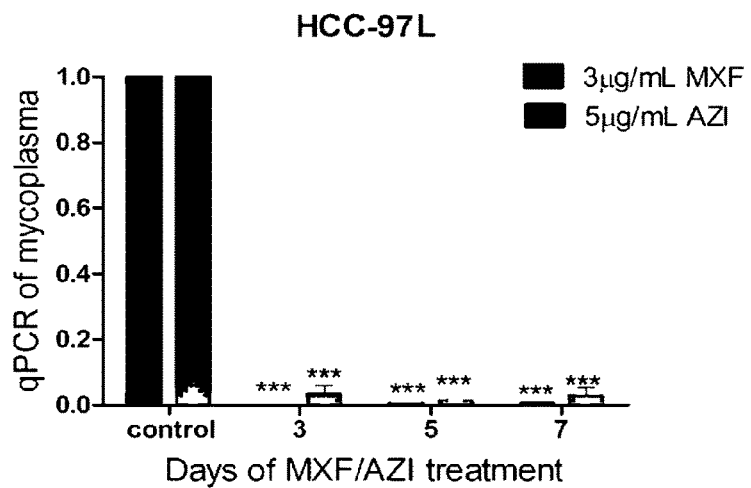
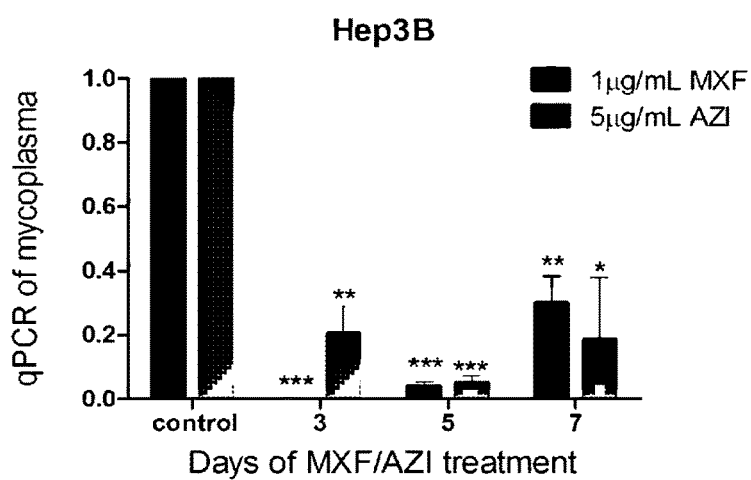
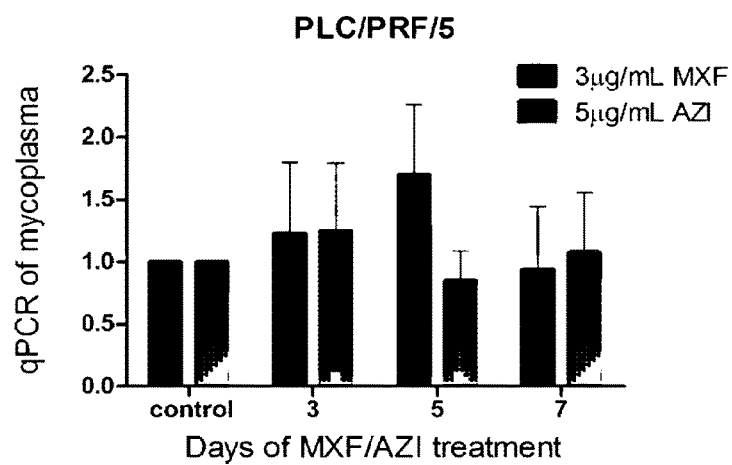
Fig.1 (Con't)

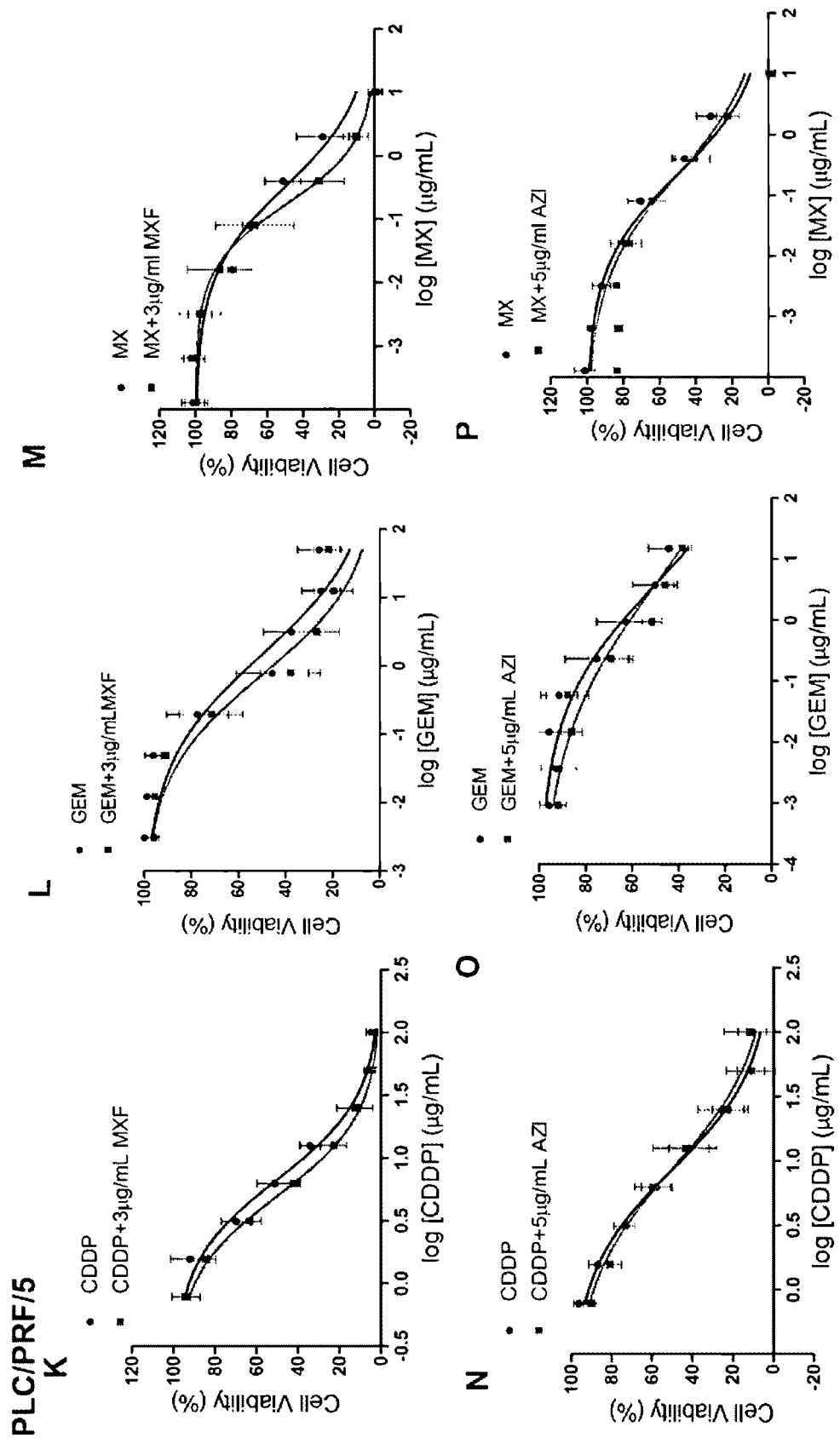
Fig.2 (Con't)

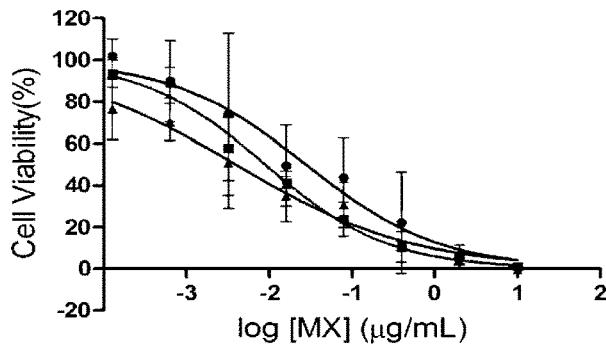
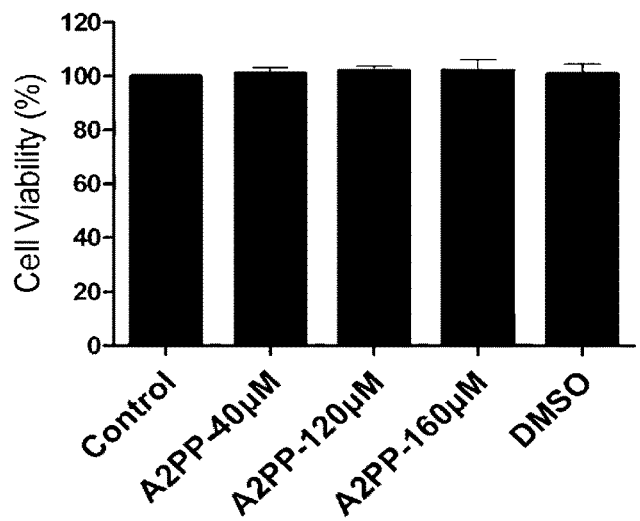
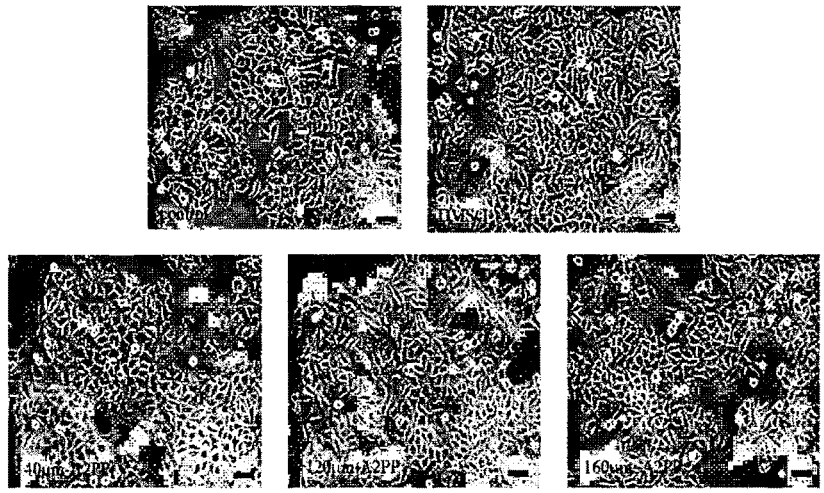
Fig.3 (Con't)

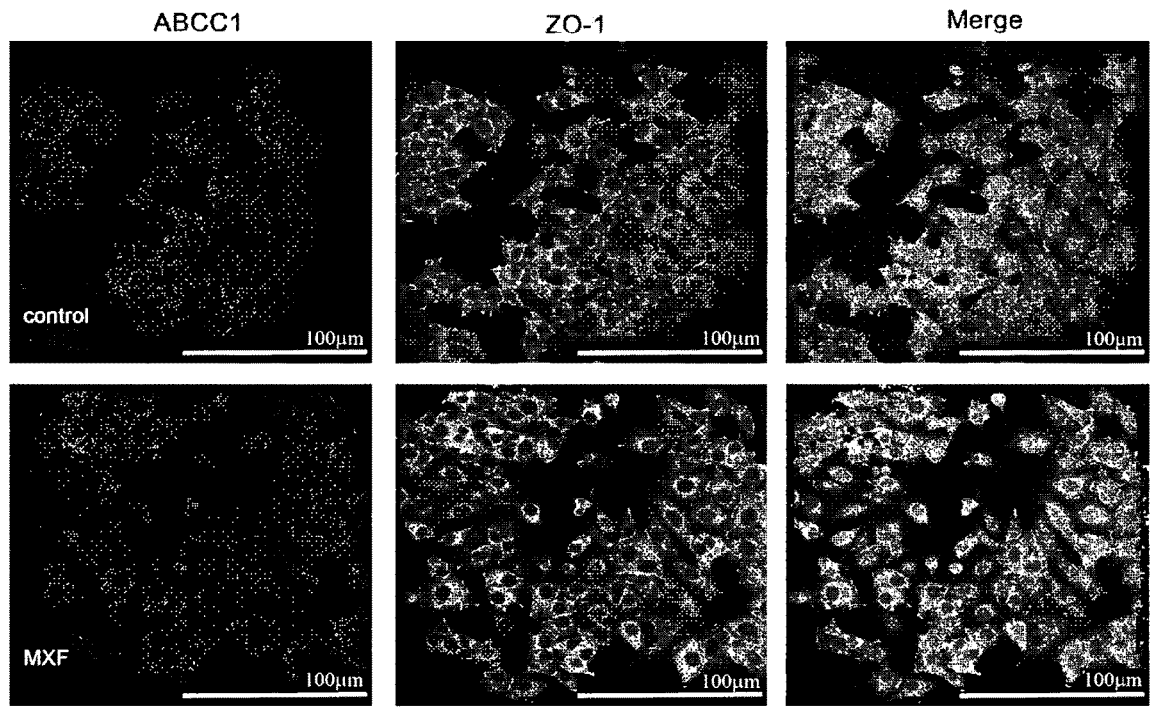
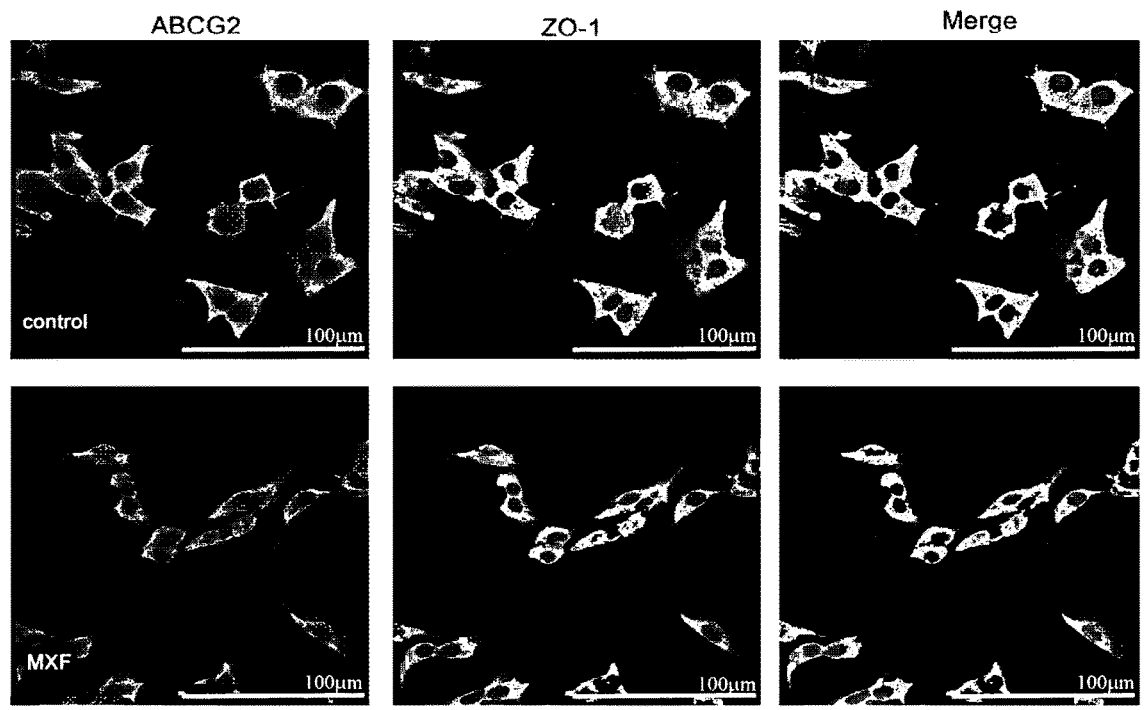
Fig.4 (Con't)

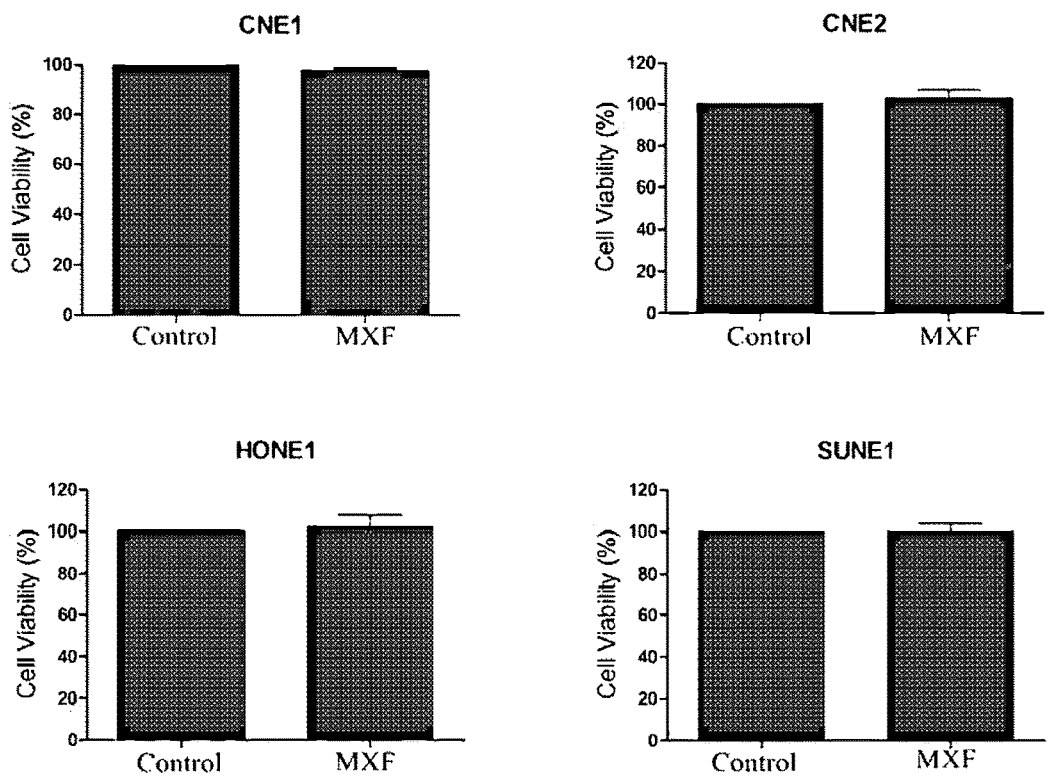
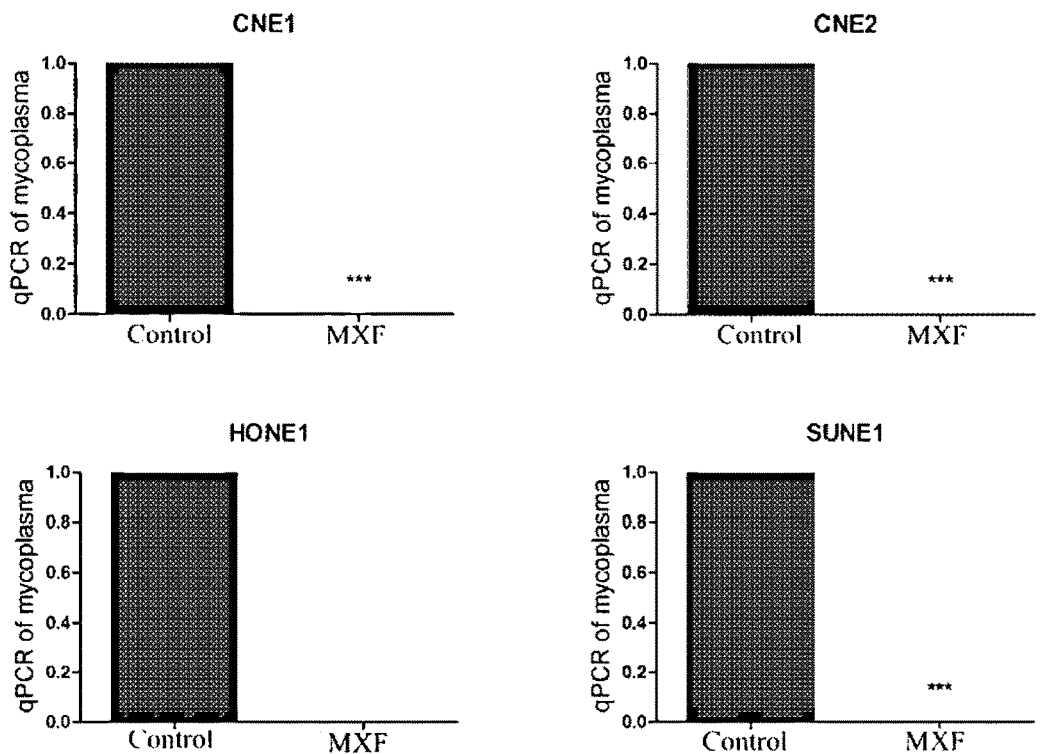
Fig.5 (Con't)

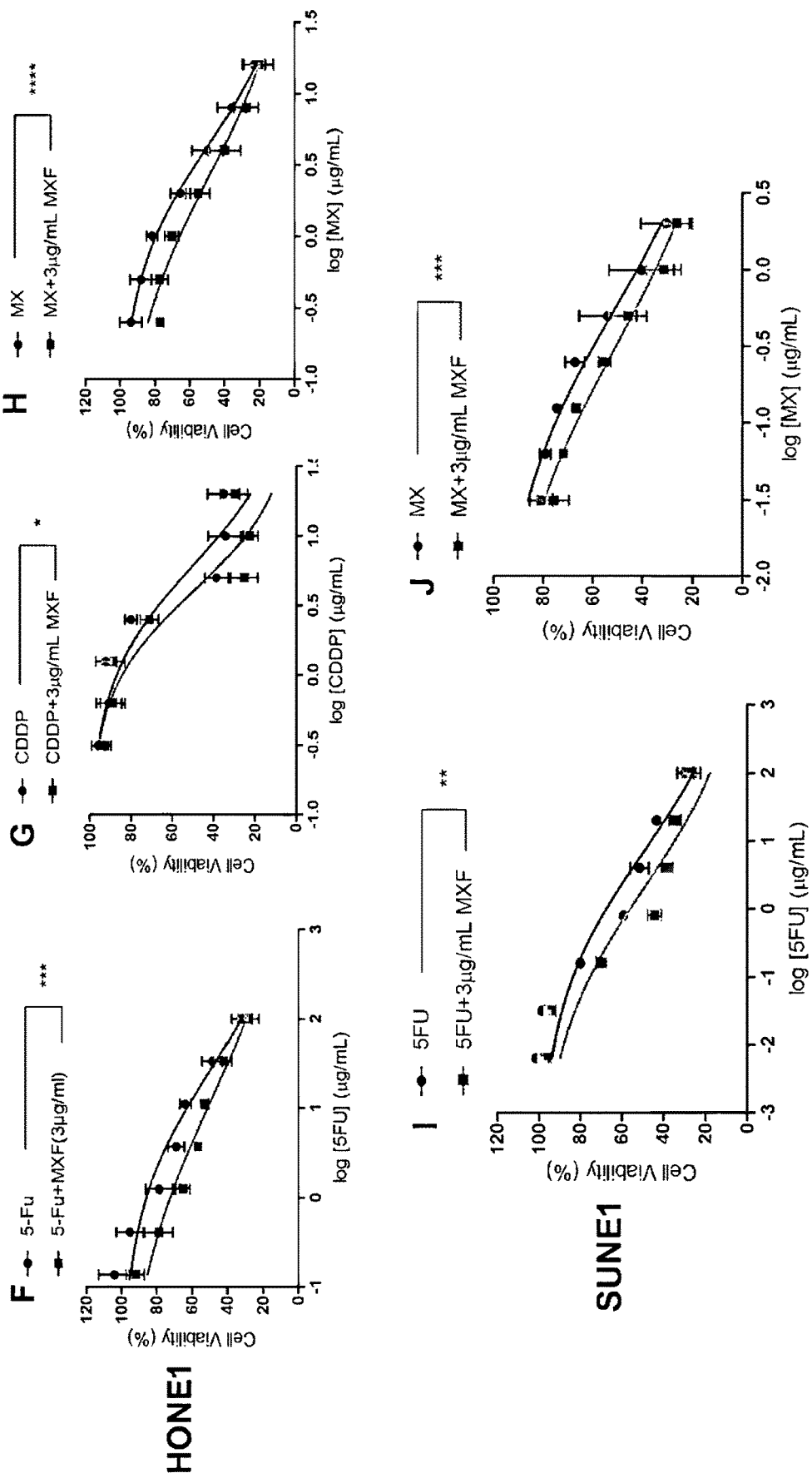
Fig.6 (Con't)

METHODS AND COMPOSITIONS FOR TREATMENT OF MULTI-DRUG RESISTANT TUMORS

CROSS-REFERENCE TO RELATED APPLICATIONS

This application is a national stage entry under 35 U.S.C. § 371 of International Patent Application No. PCT/CN2017/096331 filed Aug. 8, 2017, the entire content of which is hereby incorporated by reference.

TECHNICAL FIELD

The present invention concerns methods and compositions for treating multi-drug resistant tumors. In some aspects, the present invention is related to use of an anti-*mycoplasma* agent/blocking agent as identified herein for treating a multi-drug resistant tumor, in particular a *mycoplasma* induced multi-drug resistant tumor, in a subject.

BACKGROUND

Multidrug resistance (MDR) is a major contributor to the survival of cancer cells exposed to several drugs unrelated in both structures and mechanisms. Radio- and chemo-therapy themselves have been well known inducing cancer cell MDR, while the role of other environmental including biological factor(s) in MDR of cancers has yet to be elucidated.

*Mycoplasma* is the tiniest prokaryotic microorganism extensively existing in epithelial tissues and body cavity such as urethra, alimentary canal and respiratory tract. *Mycoplasma* has also been detected in many kinds of human carcinomas such as lung cancer, gastric carcinoma, colon carcinoma, and hepatocellular carcinoma, with known influence mainly on tumor initiation, epithelial-mesenchymal transition, migration and invasion. Recent works suggested that *mycoplasma* infection result in drug resistance to nucleoside analogues in cancer cells. However, it remains unexplored whether *mycoplasma* has effect on tumor cell sensitivity to a broader range of cytotoxic insults.

SUMMARY

In one aspect of the present invention, provided is a method for treatment of a multi-drug resistant (MDR) tumor in a subject, wherein the multi-drug resistant tumor is resistant to at least two classes of chemotherapeutic agents, the method comprising administering to the subject in need of treatment a therapeutically effective amount of an anti-*mycoplasma* agent and/or an agent blocking the interaction between membrane protein P37 of *mycoplasma* and Annexin A2 of host cells of the subject, prior to, at the same time with, or after chemotherapy.

In another aspect, the present invention provides a pharmaceutical composition for treatment of a multi-drug resistant (MDR) tumor in a subject, comprising, in unit dosage form, a therapeutically effective amount of an anti-*mycoplasma* agent and/or an agent blocking the interaction between membrane protein P37 of *mycoplasma* and Annexin A2 of host cells of the subject, a therapeutically effective amount of a chemotherapeutic agent, and a pharmaceutically acceptable carrier, wherein the chemotherapeutic agent is selected from an alkylating agent, an antibiotic, an antimetabolite, an immunotherapy, a hormone or hormone antagonist, a taxane, a retinoid, an alkaloid, an antiangiogenic agent, a topoisomerase inhibitor, a kinase inhibitor, a targeted signal transduction inhibitor, and a biological response modifier.

In a further aspect, the present invention provides a pharmaceutical kit for treatment of a multi-drug resistant (MDR) tumor in a subject, comprising, in separate dosage forms, a therapeutically effective amount of an anti-*mycoplasma* agent and/or an agent blocking the interaction between membrane protein P37 of *mycoplasma* and Annexin A2 of host cells of the subject, and a therapeutically effective amount of a chemotherapeutic agent, wherein the chemotherapeutic agent is selected from an alkylating agent, an antibiotic, an antimetabolite, an immunotherapy, a hormone or hormone antagonist, a taxane, a retinoid, an alkaloid, an antiangiogenic agent, a topoisomerase inhibitor, a kinase inhibitor, a targeted signal transduction inhibitor, and a biological response modifier.

In a yet further aspect, provided is use of an anti-*mycoplasma* agent and/or an agent blocking the interaction between membrane protein P37 of *mycoplasma* and Annexin A2 of host cells of the subject, in the preparation of a pharmaceutical composition or kit for treatment of a multi-drug resistant (MDR) tumor in a subject, wherein the multi-drug resistant tumor is resistant to at least two classes of chemotherapeutic agents.

In one or more aspects of the present invention, the agent blocking the interaction between membrane protein P37 of *mycoplasma* and Annexin A2 of host cells of the subject is an P37 inhibitor or an Annexin A2 inhibitor. In some embodiments, the P37 inhibitor is selected from an antisense oligomer selected from dsRNA, siRNA, and shRNA directed against P37 protein; and an P37 antibody or a fragment thereof. In some embodiments, the Annexin A2 inhibitor is selected from an antisense oligomer selected from dsRNA, siRNA, and shRNA directed against Annexin A2 protein; and an Annexin A2 antibody or a fragment thereof. In some embodiments, the P37 antibody is a polypeptide A2PP.

One or more aspects and features of the invention will be readily appreciable and understood from reading the following detailed description of the invention.

DETAILED DESCRIPTION

Definitions

Figure 1:
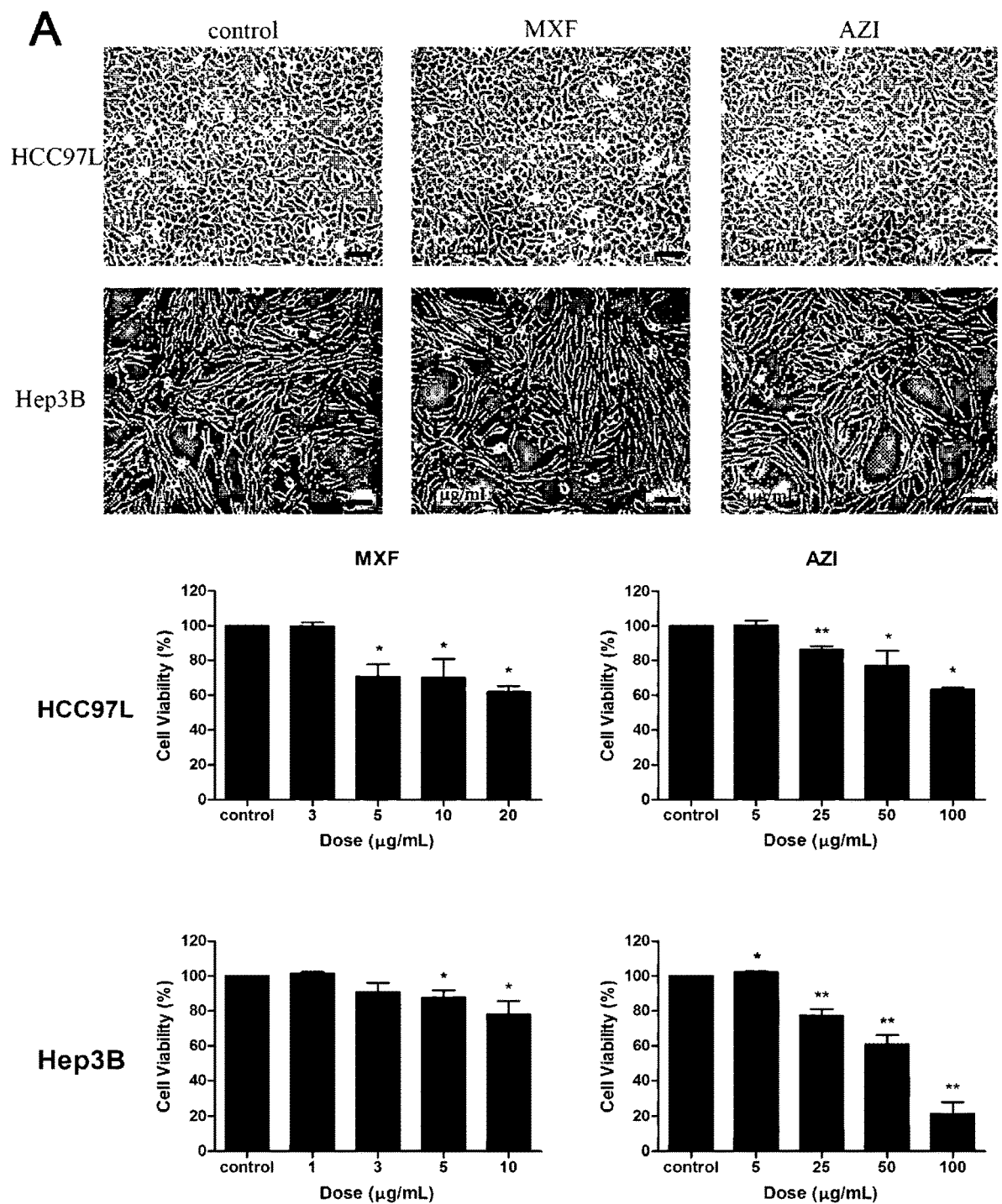
FIG. 1. The cytotoxic and anti-*mycoplasma* effect of anti-pcytoplasma antibiotics on hepatocarcinoma cells. (A) Images showed cytotoxic effect of AZI/MXF on HCC97L/Hep3B cells, respectively. (×200; bar, 50 µm); MTT analysis showed the cell viability of HCC97L/Hep3B treated with increasing concentrations of AZI/MXF, respectively. (B) The relative *mycoplasma* DNA copy numbers measured using qPCR showed the anti-*mycoplasma* effect of AZI/MXF treatment on HCC97L, Hep3B and PLC/PRF/5 cells for 3, 5 or 7 days. Error bars indicate SD of a representative experiment out of three independent experiments performed in triplicate. Statistical significance was determined by using paired two-tailed student's t-test: **P<0.0001, *P<0.001, **P<0.01, *P<0.05 as compared with control.

It is to be noted that the term "a" or "an" entity refers to one or more of that entity; for example, "an anti-*mycoplasma* agent," is understood to represent one or more anti-*mycoplasma* agents. As such, the terms "a" (or "an"), "one or more," and "at least one" can be used interchangeably herein. As used herein, the terms "treat" or "treatment" refer to both therapeutic treatment and prophylactic or preventative measures, wherein the object is to prevent or slow down (lessen) an undesired physiological change or disorder, such as the progression of cancer and development of cancer multi-drug resistance. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on. The subject herein is preferably a human.

As used herein, phrases such as "to a patient in need of treatment" or "a subject in need of treatment" includes subjects, such as mammalian subjects, that would benefit from administration of an anti-*mycoplasma* agent or composition/kit of the present disclosure used, e.g., for prophylaxis and/or for therapy.

As used herein, phrases such as "a multi-drug resistant tumor", "a multidrug resistant tumor" "a MDR tumor", "a tumor resistant to multi drugs" or "a resistant tumor" refers to a tumor or a cancer showing very low sensitivity to treatment with one or more chemotherapeutic drugs so that the symptoms thereof are not improved, relived, alleviated, or treated by the chemotherapy. In some embodiments, a MDR tumor as used herein is resistant to at least two classes of chemotherapeutic drugs that are different from each other in term of therapeutic mechanism. In some embodiments, a MDR tumor as used herein is resistant to at least two classes of chemotherapeutic agents selected from an alkylating agent, an antibiotic, an antimetabolite, an immunotherapy, a hormone or hormone antagonist, a taxane, a retinoid, an alkaloid, an antiangiogenic agent, a topoisomerase inhibitor, a kinase inhibitor, a targeted signal transduction inhibitor, and a biological response modifier. The multi-drug resistant tumor can be a tumor originally resistant to treatment with chemotherapeutic drugs. Alternatively, the multi-drug resistant tumor can be a tumor not originally resistant, but is no longer sensitive to chemotherapeutic drugs because a gene in the tumor cells is mutated due to long-term administration of the chemotherapeutic drugs or is otherwise resistant. In the present invention, the resistant tumor may be any tumor showing resistance to chemotherapeutic drug treatment, but is not specifically limited thereto. In some embodiments, the multi-drug resistant tumor is a *mycoplasma* induced MDR tumor, which means the MDR in the tumor is at least partially induced by, mediated by, or otherwise involved with *mycoplasma* infection.

As used herein, the term "tumor" refers to a malignant tissue comprising transformed cells that grow uncontrollably (i.e., is a hyperproliferative disease). Tumors include leukemias, lymphomas, myelomas, plasmacytomas, and the like; and solid tumors. Examples of solid tumors that can be treated according to the invention include but are not limited to sarcomas and carcinomas such as melanoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma.

The term "therapeutically effective amount" or "pharmaceutically effective amount" as used in this specification refers to an amount of each active ingredient that can exert clinically significant effects. The pharmaceutically effective amount of an anti-*mycoplasma* agent for a single dose may be prescribed in a variety of ways, depending on factors such as formulation methods, administration manners, age of patients, body weight, gender, pathologic conditions, diets, administration time, administration interval, administration route, excretion speed, and reaction sensitivity. For example, the pharmaceutically effective amount of an anti-*mycoplasma* agent for a single dose may be in ranges of 0.001 to 100 mg/kg, or 0.02 to 10 mg/kg, but not limited thereto. The pharmaceutically effective amount for the single dose may be formulated into a single formulation in a unit dosage form or formulated in suitably divided dosage forms, or it may be manufactured to be contained in a multiple dosage container.

As used herein, an "anti-*mycoplasma* agent" is an agent effective to treat *mycoplasma* infection including antibiotics and antioxidants. A number of different antibiotics have been used to treat *mycoplasma* infections. Macrolides such as azithromycin, clarithromycin, dirithromycin, erythromycin, josamycin, roxithromycin, spiramycin, acetylspiramycin, and telithromycin; tetracyclines such as tetracycline, doxycycline, minocycline and tigecycline may be used for treatment of *mycoplasma* infections. In some embodiments, quinolones such as ciprofloxacin, gatifloxacin, Levofloxacin, moxifloxacin, ofloxacin and sparfloxacin also have good activity against *mycoplasma*. Antioxidants, such as glutathione, may also have non-specific host immunocompetence enhancing effects and specific antiretroviral or anti-*mycoplasma* effects. Accordingly, any of the above exemplary drugs as well as other known drugs for treating human *mycoplasma* infection may be used in the present methods as anti-*mycoplasma* agents.

As used herein, the term "chemotherapy" is a category of cancer treatment that uses one or more anti-cancer drugs (chemotherapeutic agents) as part of a standardized chemotherapy regimen. Chemotherapy may be given with a curative intent (which almost always involves combinations of drugs), or it may aim to prolong life or to reduce symptoms (palliative chemotherapy). Chemotherapy is one of the major categories of the medical discipline specifically devoted to pharmacotherapy for cancer, which is called medical oncology.

The term chemotherapy as used herein is meant to include hormonal therapy and targeted therapy. Importantly, the use of drugs (whether chemotherapy, hormonal therapy or targeted therapy) constitutes systemic therapy for cancer in that they are introduced into the blood stream and are therefore in principle able to address cancer at any anatomic location in the body. Systemic therapy is often used in conjunction with other modalities that constitute local therapy (i.e. treatments whose efficacy is confined to the anatomic area where they are applied) for cancer such as radiation therapy, surgery and/or hyperthermia therapy.

In this invention, the chemotherapy is carried out by administering one or more chemotherapeutic agents selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib. The tumors to be treated by the present invention would show resistant to one or more of the chemotherapeutics as identified above without treatment by the anti-*mycoplasma* agents or the blocking agents as identified herein. The administration of the anti-*mycoplasma* agents or the blocking agents of the present invention will enhance or sensitize the response of the tumor to one or more of the chemotherapeutics.

As used herein, the phrase "an agent blocking the interaction between membrane protein P37 of *mycoplasma* and Annexin A2 of host cells" or simply "blocking agent" refers to an agent inhibiting, suppressing, reducing, intervening or excluding the interaction between P37 protein of *mycoplasma* and Annexin A2 of the subject. This can be achieved by an P37 inhibitor or an Annexin A2 inhibitor. In some embodiments, the P37 inhibitor is selected from an antisense oligomer selected from dsRNA, siRNA, and shRNA directed against P37 protein; and an P37 antibody or a fragment thereof, for example a polypeptide A2PP used in the Example of the invention. It is anticipated that an Annexin A2 inhibitor is also suitable, which can be selected from an antisense oligomer selected from dsRNA, siRNA, and shRNA directed against Annexin A2 protein; and an Annexin A2 antibody or a fragment thereof.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, genomic RNA, mRNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P-NH2) or a mixed phosphoramidate-phosphodiester oligomer.

The present invention employs, among others, antisense oligomer and similar species for use in modulating the function or effect of nucleic acid molecules encoding a P37 or Annexin A2 protein. An inhibitor of P37 or Annexin A2 protein as used herein is defined as a molecule that blocks or reduces the expression of P37 or Annexin A2 protein by interfering with transcription of the P37 or Annexin A2 gene, processing or translation of P37 or Annexin A2 mRNA or stability of P37 or Annexin A2 protein. The inhibitor can be any molecule involved in the cascade of a pathway inhibiting ATF3 expression in an MDR tumor cell. This is accomplished by providing oligonucleotides which specifically hybridize with one or more nucleic acid molecules encoding the P37 or Annexin A2 protein. As used herein, the terms "target nucleic acid" and "nucleic acid molecule encoding the protein" have been used for convenience to encompass DNA encoding the protein, RNA (including pre-mRNA and mRNA or portions thereof) transcribed from such DNA or synthesized de novo and also cDNA derived from such RNA. An oligomer of this invention that hybridizes with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of the inhibitor. In the context of the present invention, "modulation" and "modulation of expression" mean decrease in the amount or levels of a nucleic acid molecule encoding the gene, e.g., DNA or RNA. mRNA is often a preferred target nucleic acid.

In the context of this invention, "hybridization" means the pairing of complementary strands of oligomers. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense oligomer is specifically hybridizable when binding of the oligomer to the target nucleic acid interferes with the normal function of the target nucleic acid to cause a loss of activity, and there is a sufficient degree of complementarity to avoid non-specific binding of the antisense oligomer to non-target nucleic acid sequences under conditions in which specific binding is desired, i.e., under physiological conditions in the case of in vivo assays or therapeutic treatment, and under conditions in which assays are performed in the case of in vitro assays.

It is understood in the art that the sequence of an antisense oligomer need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense oligomer are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligomer which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

In one or more aspects of the present invention, the multi-drug resistant tumor is a *mycoplasma*-induced MDR tumor. In some embodiments, the tumor is selected from a group consisting of melanoma, fibrosarcoma, hepatocellular carcinoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, nasopharyngeal carcinoma, Ewing's tumor, leiomyosarcoma, rhabdomyosarcoma, gastric carcinoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma.

Methods and Therapies

One aspect of the invention is related to methods for treating a multi-drug resistant tumor in a subject. The methods comprise administering to the subject in need thereof a therapeutically effective amount of an anti-*mycoplasma* agent, prior to, at the same time with, or after chemotherapy. In some embodiments, the methods comprise administering to the subject in need thereof a therapeutically effective amount of an agent blocking the interaction between membrane protein P37 of *mycoplasma* and Annexin A2 of host cells of the subject, prior to, at the same time with, or after chemotherapy. In the present methods, the anti-*mycoplasma* agent/blocking agent and the chemotherapy are administered in combination. In one embodiment, the administration of the anti-*mycoplasma* agent/blocking agent is performed prior to the chemotherapy. In another embodiment, the administration of the anti-*mycoplasma* agent/blocking agent and the chemotherapy is performed simultaneously. In another embodiment, the administration of the anti-*mycoplasma* agent/blocking agent is performed after the chemotherapy.

In certain embodiments, the anti-*mycoplasma* agent/blocking agent is administered orally. In certain embodiments, the anti-*mycoplasma* agent/blocking agent is administered parenterally, e.g. intravenously, intramuscularly, percutaneously or intracutaneously.

In certain embodiments, the methods of treating a MDR tumor prevent progression of the tumor and/or the onset of disease caused by the tumor. Thus, in some embodiments, a method for preventing the progression of a MDR tumor and/or the onset of disease caused by a MDR tumor, comprising administering of an effective amount of an anti-*mycoplasma* agent/blocking agent to a subject in need thereof is provided. In certain embodiments, the methods consist of treating a MDR tumor to prevent the onset, progression and/or recurrence of a symptom associated with the tumor. In certain embodiments, a method is provided for preventing a symptom associated with a MDR tumor in a subject, comprises administering an effective amount of an anti-*mycoplasma* agent/blocking agent to a subject in need thereof.

In some embodiment, the methods of the present invention can be used for prophylaxis purpose. For example, in one embodiment, the subject is identified of *mycoplasma* infection in a tumor. The subject is suffering or may have the risk to suffer from a multidrug resistance to chemotherapy. The subject is administered the anti-*mycoplasma* agent/blocking agent of the present invention so as to eliminate the *mycoplasma* infection in the tumor, in an aim to prevent the occurrence of a multidrug resistance. Identification of *mycoplasma* infection in a tumor in a subject can be performed by techniques well-known in the art, for example PCR-based techniques as widely available in the market.

The present invention also speculates a use of the anti-*mycoplasma* agent/blocking agent as identified in the present invention in the manufacturing of a pharmaceutical composition or pharmaceutical kit for treatment of a multidrug resistant tumor, in particular a *mycoplasma* induced multidrug resistant tumor, in a subject. The present invention further speculates a use of the anti-*mycoplasma* agent/blocking agent as identified in the present invention for treatment of a multidrug resistant tumor, in particular a *mycoplasma* induced multidrug resistant tumor, in a subject.

Compositions/Kit

Another aspect of the present invention provides a pharmaceutical composition in unit dosage form, comprising a therapeutically effective amount of the anti-*mycoplasma* agent/blocking agent of the present invention, a therapeutically effective amount of one or more chemotherapeutics, and a pharmaceutically acceptable carrier. The pharmaceutical composition is intended for treatment of a MDR tumor in a subject. The anti-*mycoplasma* agent/blocking agent and the one or more chemotherapeutics may be prepared in a suitable pharmaceutically acceptable carrier or excipient. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologies standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

In another aspect, the present invention provides a pharmaceutical kit comprising a therapeutically effective amount of the anti-*mycoplasma* agent/blocking agent of the present invention and a therapeutically effective amount of one or more chemotherapeutics, each in separate dosage form. In one embodiment, the pharmaceutical kit comprises, in one compartment, a therapeutically effective amount of the anti-*mycoplasma* agent and a pharmaceutically acceptable carrier, and, in another compartment, a therapeutically effective amount of one or more chemotherapeutics and a pharmaceutically acceptable carrier. In one embodiment, the pharmaceutical kit comprises, in one compartment, a therapeutically effective amount of the blocking agent and a pharmaceutically acceptable carrier, and, in another compartment, a therapeutically effective amount of one or more chemotherapeutics and a pharmaceutically acceptable carrier. Alternatively, in some embodiments, the pharmaceutical kit includes the two dosage forms in a same compartment. In some embodiment, the anti-*mycoplasma* agent/blocking agent is in a same dosage form with that of the chemotherapeutic, for example both being oral dosage form, such as a tablet. In some embodiment, the anti-*mycoplasma* agent/blocking agent is in a different dosage form from that of the chemotherapeutic, for example with the former in an injectable form and the latter in an oral dosage form. The dosage forms of the anti-*mycoplasma* agent/blocking agent and the one or more chemotherapeutics depend on the respective pharmacological properties, the desired administration routes, and so on. The pharmaceutically acceptable carrier is identified as above.

Examples

The present inventors found that the sensitivity of hepatocarcinoma cells to Cisplatin, Gemcitabine and Mitoxantrone was increased by *mycoplasma* elimination. Parallel to the effect of anti-*mycoplasma* agent, interrupting the interaction between *Mycoplasma hyorhinis* membrane protein P37 and Annexin A2 of host cells using the N-terminal of Annexin A2 polypeptide enhanced the sensitivity of HCC97L cells to Gemcitabine and Mitoxantrone. These results suggest that *mycoplasma* induces a resistance to multiple drugs in hepatocarcinoma cells which requires the interaction between P37 and Annexin A2. Similar enhancement of sensitivity to Cisplatin, fluorouracil and Mitoxantrone was reproduced by anti-*mycoplasma* treatment in nasopharyngeal carcinoma cells.

Two antibiotics with totally different mechanisms to contain *mycoplasma* in cancer cells: Moxifloxacin (MXF), a fluoroquinolones which inhibits topoisomerase, and azithromycin (AZI), a macrolides which targets ribosome for protein synthesis in bacterium, were used. The hepatocarcinoma cells were then treated with an alkylating agent, Cisplatin (CDDP), an antimetabolic anticarcinoma agent, Gemcitabine (GEM), and an anthracycline topoisomerase inhibitor, Mitoxantrone (MX), respectively with or without the existence of non-cytotoxic concentration of MXF or AZI. To identify the real origin of the enhanced cytotoxicity from anti-tumor treatment combined with MXF or AZI, evidences were pooled together for analysis: (1) MXF and AZI were introduced at non-cytotoxic concentrations; (2) in cell lines where *mycoplasma* was cleaned up by MXF and AZI, cytotoxicity of anti-tumor drugs was intensified; (3) in cell line where *mycoplasma* survived MXF and AZI, cytotoxicity of anti-tumor drugs remained unchanged. It thus can be reasoned out that the presence of *mycoplasma* is the driving force of a MDR in those tumor cells, and the MDR can be removed through the elimination of *mycoplasma*, leading to the augmentation of the anti-tumor activity of chemotherapeutic agents. In nasopharyngeal carcinoma cells, anti-*mycoplasma* treatment enhanced the cellular sensitivity to CDDP, MX and another antimetabolic anticarcinoma agent fluorouracil (5-FU) as well.

*Mycoplasma* membrane protein P37 is a functional protein intensively studied for its role in tumor behaviors. Recent data indicated that P37 promoted tumor progression through its interaction with N-terminal of Annexin A2 (ANXA2) in host cells, while P37 antibodies, a polypeptide A2PP (a 30 amino acids polypeptide within the N-terminal of ANXA2), and anti-*mycoplasma* reagent like MYCO I, were able to block this interaction. The inventors demonstrated here that non-cytotoxic levels of A2PP improved the sensitivity of tumor cells to chemotherapeutic drugs, very similar to the effect of *mycoplasma* removal. This result clearly indicates that the interaction of P37 and ANXA2 is the initial step of the MDR induced by *mycoplasma*, and interrupting this interaction in cancer cells restored their sensitivity to chemotherapeutic agents.

Materials and Methods

Drugs and Reagents:

Fluorouracil (5-FU) injection was purchased from Shanghai Xudonghaipu Pharmaceutical Co., Ltd. (Shanghai, China). Cisplatin (CDDP) was purchased from Hospira Australia Pty Ltd. (Victoria, Australia). Gemcitabine Hydrochloride for Injection (GEM) was purchased from Eli Lilly and Company (Indiana, USA). Mitoxantrone Hydrochloride Injection (MX) was purchased from Sichuan Shenghe Pharmaceutical Co., Ltd. (Sichuan, China). Moxifloxacin Hydrochloride and Sodium Chloride Injection (MXF) were purchased from Bayer Ltd. (Leverkusen, Germany). Azithromycin for Injection (AZI) was purchased from Pfizer (Nk, USA). The primary antibodies were rabbit monoclonal ABCB1 antibody (Cell Signaling Technology, Sydney, Australia), rabbit monoclonal ABCC1 antibody (Cell Signaling Technology, Sydney, Australia), and mouse monoclonal ABCG2 antibody (Santa Cruz Biotechnology, Texas, USA). Mouse monoclonal β-actin antibody (Thermo Fisher Scientific, MA, USA) was used as an internal reference. Mouse monoclonal ZO-1 antibody (Thermo Fisher Scientific, MA, USA) and rabbit polyclonal ZO-1 antibody (Thermo Fisher Scientific, MA, USA) were used to delimitate the membrane in immunofluorescence. Secondary antibodies were horse anti-mouse/rabbit IgG-horseradish peroxidase (Cell Signaling Technology, Sydney, Australia) for Western blotting. Alexa Fluor-conjugated anti-rabbit and Alexa Fluor-conjugated anti-mouse secondary antibodies (Thermo Fisher Scientific, MA, USA) were used for immunoflourescence.

Cell Culture:

The human liver cancer cell line HCC97L was obtained from Zhongshan Hospital Affiliated to Fudan University (Shanghai, China). Hep3B and PLC/PRF/5 cell lines were obtained from American Type Culture Collection (ATCC, Manassas, USA). The nasopharyngeal carcinoma (NPC) cell lines CNE1 and CNE2 were obtained from Experimental Animal Center of Sun Yat-sen University (Guangzhou, China). HONE1 and SUNE1 cell lines were gifts from Prof. Ma Jun (Cancer Center of Sun Yat-sen University). CNE1, CNE2, HONE1, SUNE1, HCC97L and Hep3B were cultured in RPMI 1640 medium (Corning, N.Y., USA) while PLC/PRF/5 in DMEM (Corning, N.Y., USA) containing 10% fetal bovine serum (FBS, Biowest, Nuaillé, France), 100 U/mL penicillin, and 100 U/mL streptomycin (PAN-Biotech GmbH, AidenbachBavaria, Germany). All the cells were incubated at 37° C. with 5% $CO_2$ and 95% relative humidity. *Mycoplasma* Detection Using Quantitative Real-Time PCR:

Total DNA was extracted from $5 \times 10^5$ cells from each group by digestion at 70° C. for 10 min in 0.5% Tween-20, 50 mM Tris (pH 8.5), 1 mM EDTA, and 200 mg/L proteinase K, followed by phenol/chloroform/isoamyl alcohol extraction and sodium acetate precipitation. DNA precipitates were washed with 70% ethanol, dried, and dissolved in 20 μL of sterile water. The extracted DNA (14, 1.2 μg) from the cells was added to 94 of the reaction solution, containing PCR buffer (SuperRealPreMix, SYBR Green; Tiangen Biotech, Beijing, China) and primers pairs for *mycoplasma* detection and reference control (β-actin) with a final concentration of 0.12 μM for each primer, to a total volume of 10 μL. Quantitative real-time PCR (qPCR) was performed as the following profile: 95° C. for 1 min (preincubation), followed by 40 cycles at 95° C. for 10 s (denaturation), 60° C. for 30 s (annealing and elongation). The primers (Table 1) for *mycoplasma* detection were gifts from Prof. Zhongning Lin (School of Public Health, Xiamen University) including two forward primers for universal mycoplasmal detection, one forward primer to detect *Myco M. pirum.*, one for *Myco A. laidlawii.* detection and a mix of degenerate primers to work as the reverse primers.

TABLE 1

Primers used for qPCR of Mycoplasma detection.

| Primers | Sequences |
| --- | --- |
| β-actin (F) | 5'-GATCATTGCTCCTCC TGAGC-3' |
| β-actin (R) | 5'-ACTCCTGCTTGCTGA TCCAC-3' |
| Myco 6Mix.A (F) | 5'-TCTGAAT<u>C</u>TGCCGGG ACCACC-3' |
| Myco 6Mix.B (F) | 5'-TCTGAAT<u>TT</u>GCCGGG ACCACC-3' |
| Myco M. pirum. (F) | 5'-GGAAAATGTTATTTT GACGGAACCT-3' |
| Myco A. laidlawii. (F) | 5'-GGAATCCCGTTTGAA GATAGGA-3' |
| Myco 8Mix. (R) | 5'-CTTTCC(A/C)TCAC (G/T)GTACT(A/G)GTT CACT-3' |

F: forward primer; R: reverse primer.

Figure 2:
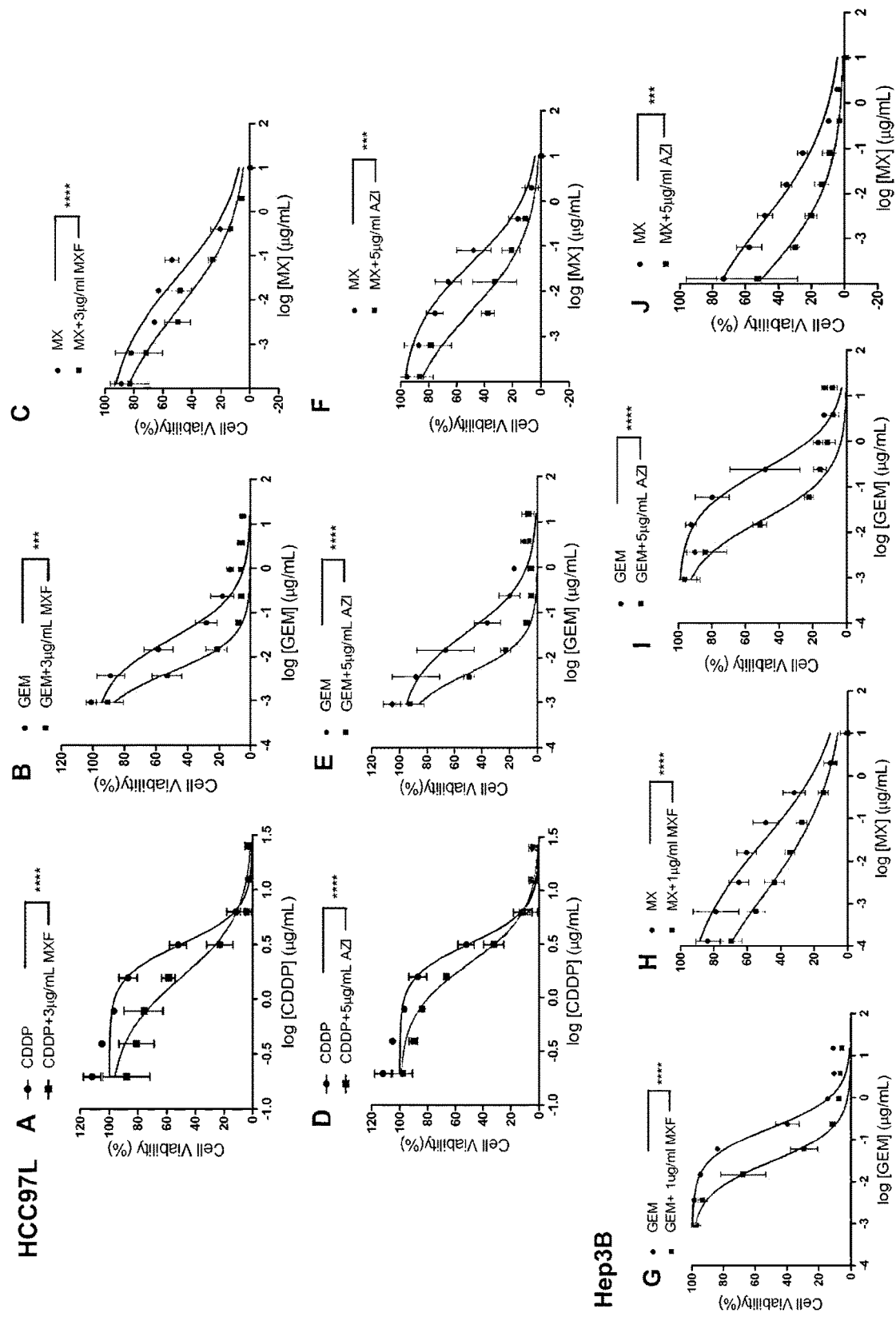
FIG. 2. The cell viability of hepatocarcinoma cells treated with different chemotherapeutic drugs alone or with the presence of anti-pcytoplasma antibiotics. Cell viability of HCC97L (A/B/C and D/E/F), Hep3B (G/H and I/J) and PLC/PRF/5 cell (K/L/M and N/O/P), which were treated with CDDP, GEM and MX with or without MXF/AZI at the indicated concentrations. Error bars indicate SD of a representative experiment out of three independent experiments performed in triplicate. Statistical testing was performed by comparing the log $EC_{50}$ values by means of an extra-sum-of-squares F test. **$P<0.0001$, *$P<0.001$, **$P<0.01$, *$P<0.05$ as compared to the chemotherapeutic drug alone controls.
Figure 3:
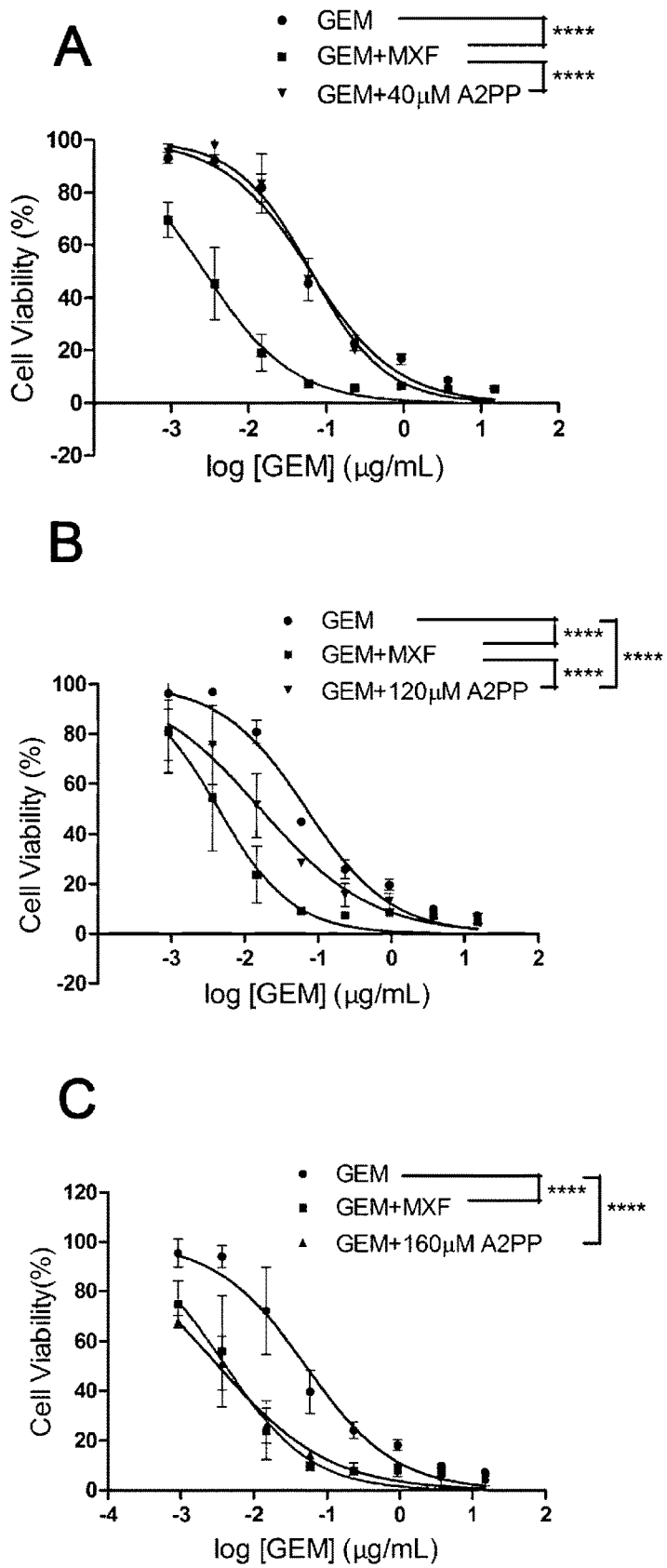
FIG. 3. The effect of A2PP on the sensitivity of HCC97L to chemotherapeutic drugs. (A, B and C) Cell viability of HCC97L cells treated using GEM alone, GEM with the presence of MXF or GEM with increasing concentrations of A2PP. (D) Cell viability of HCC97L cells treated using MX alone, MX with the presence of MXF or MX with 160 μM of A2PP. Statistical testing was performed by comparing the log $EC_{50}$ values by means of an extra-sum-of-squares F test. **$P<0.0001$, *$P<0.001$, **$P<0.01$, *$P<0.05$ as compared with each group. (E) Cell viability of HCC97L cells treated with different concentrations of A2PP or vehicle DMSO for 72 h (×200; bar, 50 μm). Statistical significance was determined by using paired two-tailed student's t-test. Error bars indicate SD of a representative experiment out of three independent experiments performed in triplicate.
Figure 6:
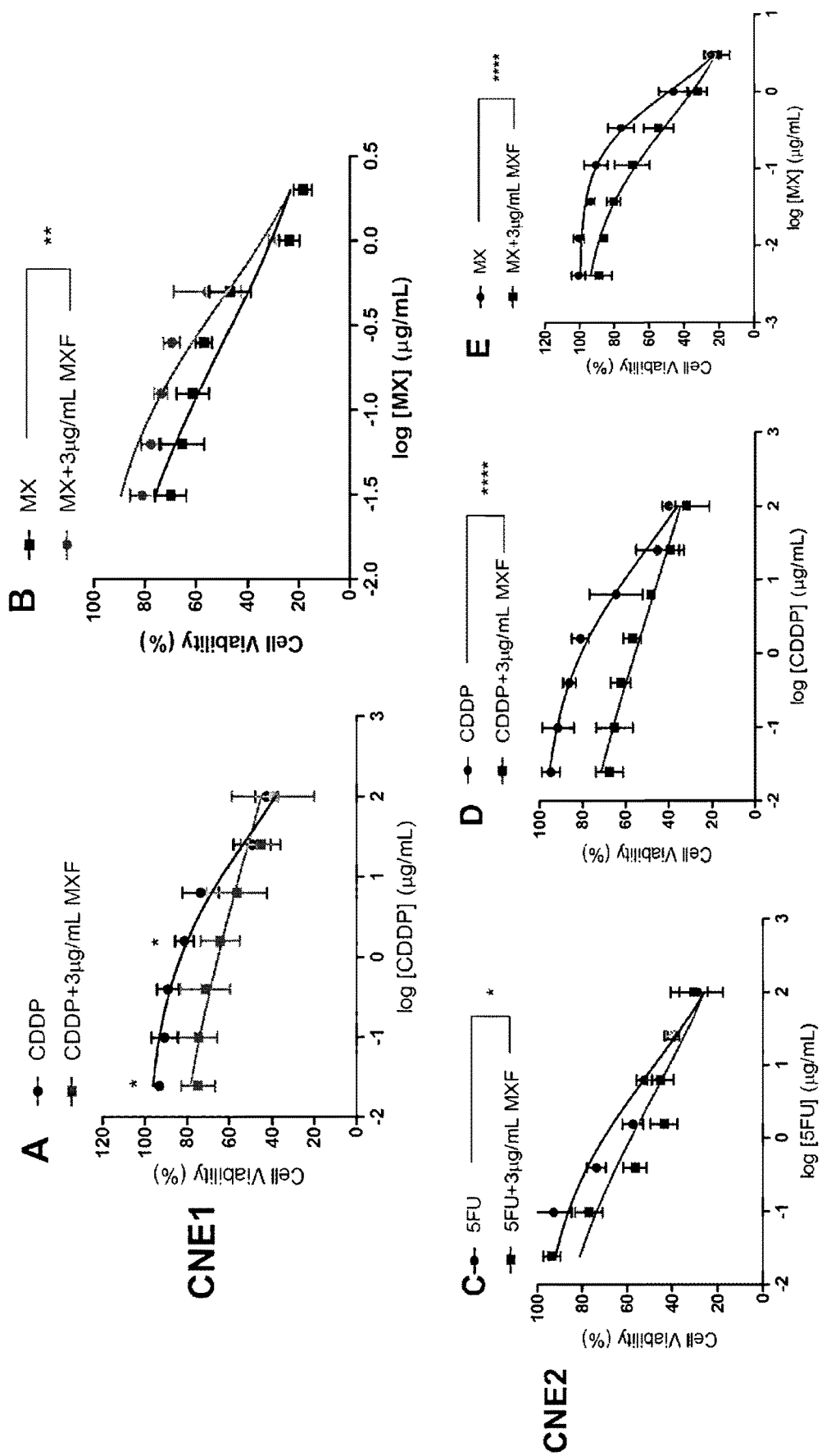
FIG. 6. The cell viability of NPC cell lines treated with different chemotherapeutic drugs alone or with the presence of MXF. Cell viability of CNE1 (A and B), CNE2 (C, D and E), HONE1 (F, G and H) and SUNE1 (I and J), which were treated with 5-FU/CDDP/MX with or without MXF at the indicated concentrations. Error bars indicate SD of a representative experiment out of three independent experiments performed in triplicate. Statistical testing was performed by comparing the log $IC_{50}$ values by means of an extra-sum-of-squares F test with an exception made in (A) where two-tailed student t-test was employed. **$P<0.0001$, *$P<0.001$, **$P<0.01$, *$P<0.05$ as compared to the chemotherapeutic drug alone controls.

Drug Treatment and Cytotoxicity Assay:

HCC97L, Hep3B and PLC cells were pretreated with 3 μg/mL (or 11.1 g/mL for Hep3B cell line) MXF or 5 μg/mL AZI respectively for 5 days. CNE1, CNE2, HONE1 and SUNE1 were treated with 3 μg/mL MXF for 7 days. Then, HCC97L ($3 \times 10^3$ well$^{-1}$), Hep3B ($4 \times 10^3$ well$^{-1}$), PLC ($4 \times 10^3$ well$^{-1}$), CNE1 ($1.75 \times 10^3$ well$^{-1}$), CNE2 ($3.5 \times 10^3$ well$^{-1}$), HONE1 ($2 \times 10^3$ well$^{-1}$) and SUNE1 ($2 \times 10^3$ well$^{-1}$) were seeded in 96-well plates (1004/well) and allowed to attach for 24 h. After that, human liver cancer cell lines were treated with 3 chemotherapeutic drugs separately at different concentrations (as indicated in FIG. 2) in the presence of the anti-*mycoplasma* antibiotics for 48 h. NPC cell lines were treated with 4 chemotherapeutic drugs separately at different concentrations (as indicated in FIG. 6) in the presence of MXF for 48 h. In the P37-ANXA2 interruption experiment, A2PP was dissolved in DMSO and HCC97L cells were pretreated with A2PP (as indicated in FIG. 3) 24 h before GEM or MX treatment. 104 of MTT (5 mg/ml final concentration; MP Biomedicals, LLC, CA, USA) was added to each well. After 4 h incubation at 37° C., the medium was removed and 100 μL/well DMSO (GBCBIO Technologies, Guangzhou, China) was added. The plates were mixed by a thermomixer for 5 min at RT. Absorbance measures were made in a microplate reader (iMark, Bio-Rad Laboratories, CA, USA) at 570/655 nm.

Western Blot:

Cells were washed by ice-cold PBS and lysed in Tris-NaCl buffer (50 mM Tris pH 7.4, 150 mM NaCl, 25 mM EDTA, 1 mM NaF, Protease Inhibitor Cocktail, 1 mM PMSF and 1% Triton X-100) on ice for 20 min. Then the lysate was centrifuged at 12000 rmp for 15 min at 4° C. Protein concentration was determined using Thermo Scientific Pierce BCA protein assay kit (Pierce, Rockford, Ill., USA) according the manufacturer's recommendation. For protein separation, equal amounts of protein (30 μg) were separated by 8% SDS-polyacrylamide gel electrophoresis and transferred onto polyvinylidene difluoride membranes (Millipore Corporation, MA, USA). The blots were blocked in 5% skim milk for 1 h at RT and incubated overnight with primary antibodies at 4° C., followed by incubating with secondary antibodies for 1 h at RT. The blots were washed three times with TBS-T, each for 5 min, and incubated with Western Lightning Chemiluminescence Reagent Plus ECL kit (Amersham, USA) for 1 min to measure the protein expression. Protein band densitometry was performed using ImageJ software (National Institutes of Health).

Immunoflourscence Staining:

Cells were cultured and treated directly in chamber slides and were fixed with 4% formaldehyde for 15 min at RT. After rinsing slides three times in PBS for 5 min each, cells were blocked in 5% BSA for 1 h. Primary antibodies were applied to the cells overnight at 4° C., followed by fluorochrome-conjugated secondary antibodies and Hoechst33342 1-2 h at room temperature in the dark. A Nikon A1 confocal system (Nikon, Tokyo, Japan) was used to observe the location of indicated proteins. Digital images were arranged by Adobe Photoshop CS4 (Adobe Systems).

Statistical Analysis:

All the experiments were performed 3 times. All data were presented as mean±SD. Paired two-tailed student's t-test was used for comparison between two groups, extra-sum-of-squares F tests was used for dose-response curves (except for FIG. 6A as indicated in the figure legend), and all performed using GraphPad PRISM 5 (GraphPad Software, San Diego, Calif., USA). The significance level was set at $P<0.05$. No randomization or blinding was used in the studies.

Results

Moxifloxacin and Azithromycin Eliminated *Mycoplasma* in Human Hepatocellular Carcinoma Cells.

Cells were treated with two antibiotics: a macrolide agent, Azithromycin (AZI), and a fluoroquinolone agent, Moxifloxacin (MXF). Cell morphology and MTT assay showed that 3 g/mL MXF and 5 g/mL AZI were non-toxic to HCC97L cells as well as 1 g/mL MXF and 5 g/mL AZI to Hep3B (FIG. 1A). Real Time PCR analysis indicated that 1 g/mL and 3 g/mL MXF eradicated *mycoplasma* completely in Hep3B and HCC97L cells respectively, while 5 g/mL AZI removed *mycoplasma* significantly in both cell lines. In PLC/PRF/5 cell line, however, *mycoplasma* remained intact under the treatment of 3 g/mL MXF or 5 g/mL AZI (FIG. 1B).

Moxifloxacin and Azithromycin Enhanced the Sensitivity of Hepatocellular Carcinoma Cells to Chemotherapeutic Drugs.

The cells were then treated with an alkylating agent, Cisplatin (CDDP), an antimetabolic anticarcinoma agent, Gemcitabine (GEM), and an anthracycline topoisomerase inhibitor, Mitoxantrone (MX), respectively with or without the existence of non-cytotoxic concentration of MXF or AZI. The results of MTT assay indicated that the sensitivity of HCC97L cells to CDDP, GEM and MX, and the sensitivity of Hep3B cells to GEM and MX were enhanced by MXF and AZI. In PLC/PRF/5 cell line, neither MXF nor AZI improved the efficacy of the anti-tumor drugs (FIG. 2).

*Mycoplasma*-Related MDR Required the Interaction of P37 and Annexin A2.

To explore the initiation of infection-related MDR, we employed A2PP to trap the P37 protein from binding ANXA2. With the presence of the increasing concentration of A2PP, GEM exerted stronger inhibiting effect than treated alone in HCC97L cell line. Impressively, the maximum effect of GEM with A2PP was equivalent to that with MXF (FIGS. 3A, B and C). This enhancement by A2PP was reproduced when used together with MX (FIG. 3D). In addition, cell morphology and MTT assay showed that A2PP had no impact on cell survival (FIG. 3E), indicating that the augmentation of the anti-tumor effect by A2PP could not result from its direct cytotoxicity.

ABC Transporters were not Involved in *Mycoplasma*-Related MDR.

Figure 4:
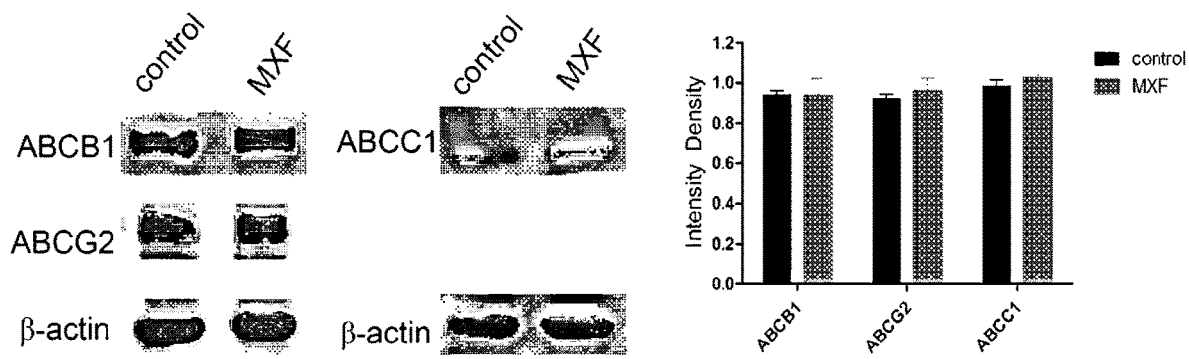
FIG. 4. The expression and subcellular location changes of ABC transporter family proteins with or without MXF treatment. (A) Protein expressions of ABCB1, ABCC1 and ABCG2 in HCC-97L cells treated with MXF for 7 days compared with non-treated controls. Statistical significance was determined by using unpaired two-tailed student's t-test. Error bars indicate SD of a representative experiment out of three independent experiments performed in triplicate. The subcellular locations of ABCB1 (B), ABC1 (C) and ABCG2 (D) in HCC-97L cells treated with MXF for 7 days or non-treated controls. ZO-1 was used to delimitate the membrane (×400; bar, 100 μm).
Figure 4:
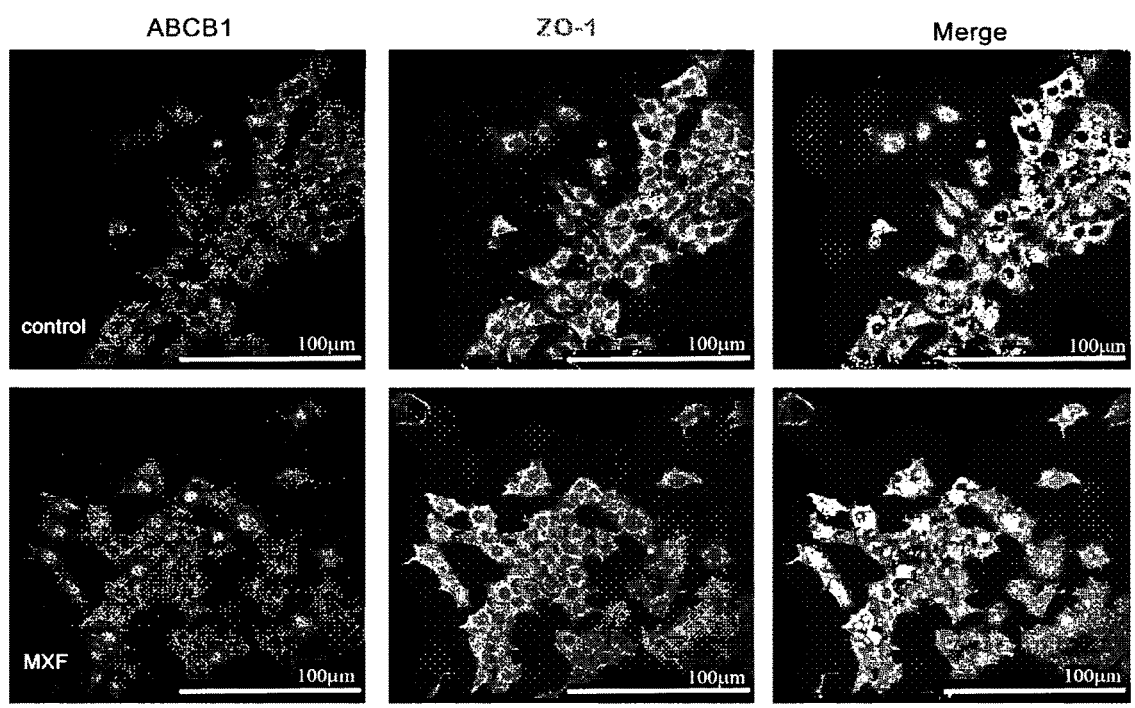

To figure out the cellular effector responsible for the *mycoplasma*-related MDR, we measured the expression and sub-cellular location of three ABC transporter members: ABCB1, ABCC1 and ABCG2. Interestingly, no substantial change in protein quantity of these transporters was observed with MXF treatment. The distribution of these proteins on cell membrane did not alter either (FIG. 4).

Moxifloxacin Eliminated *Mycoplasma* in Human Nasopharyngeal Carcinoma Cells.

Figure 5:
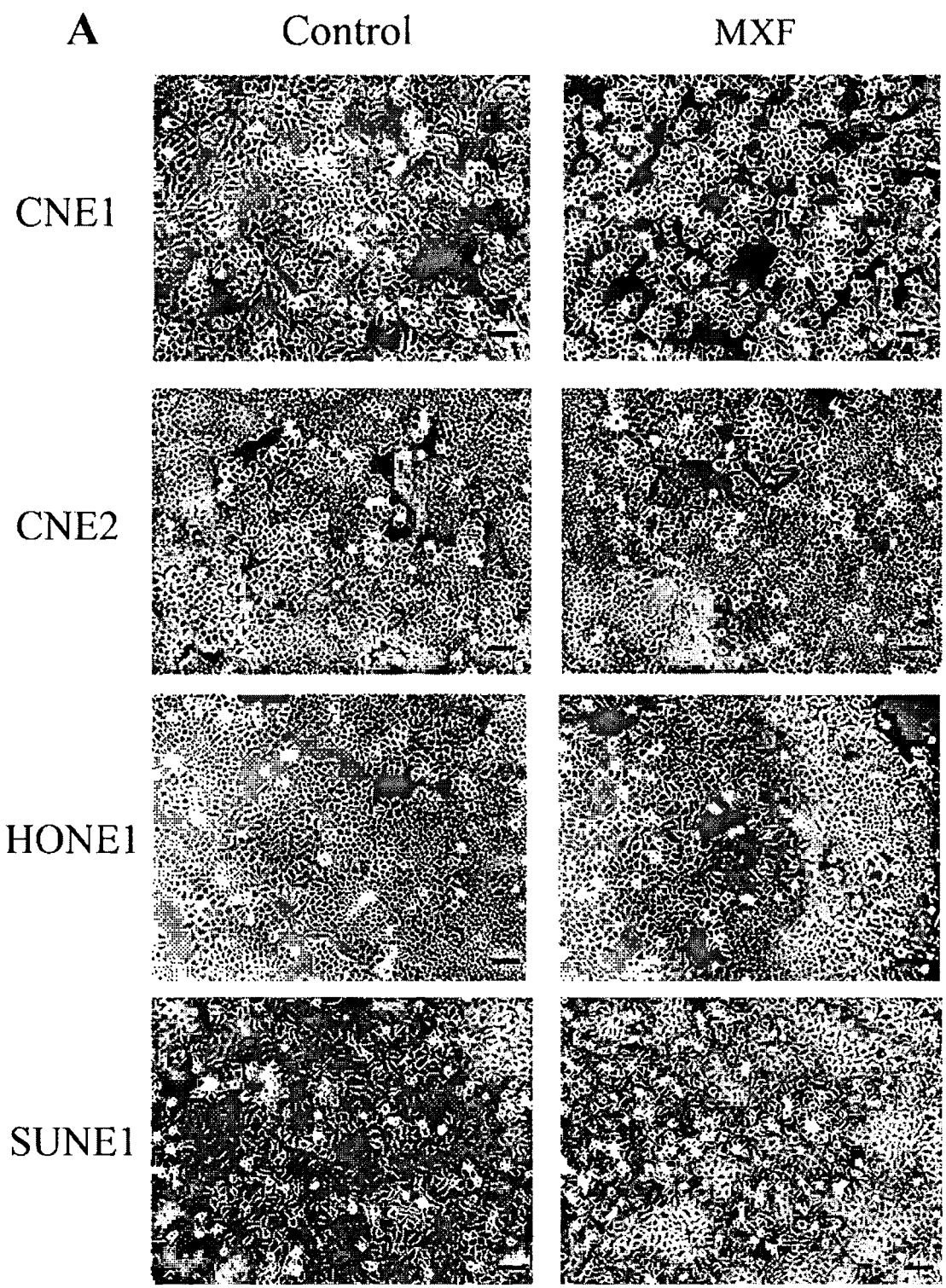
FIG. 5. The cytotoxic and anti-*mycoplasma* effect of anti-*mycoplasma* antibiotics on nasopharyngeal carcinoma cells. (A) Images showed cytotoxic effect of MXF on CNE1/CNE2/HONE1/SUNE1 cells. (×100; bar, 100 μm); (B) MTT analysis showed the cell viability of CNE1/CNE2/HONE1/SUNE1 cells treated with 3 μg/mL MXF. (C) The relative *mycoplasma* DNA copy numbers measured using qPCR showed the anti-*mycoplasma* effect of MXF treatment on CNE1/CNE2/HONE1/SUNE1 cells for 7 days. Error bars indicate SD of a representative experiment out of three independent experiments performed in triplicate. Statistical significance was determined by using paired two-tailed student's t-test: *$P<0.001$, *$P<0.01$, *$P<0.05$ as compared with control.

Cell morphology and MTT assay showed that 3 g/mL MXF were non-toxic to NPC cells of CNE1, CNE2, HONE1 and SUNE1 cell lines (FIG. 5A, 5B). Real Time PCR analysis indicated that 3 g/mL MXF eradicated *mycoplasma* completely in all four NPC cell lines (FIG. 5C).

Moxifloxacin Enhanced the Sensitivity of Nasopharyngeal Carcinoma Cells to Chemotherapeutic Drugs.

We then treated NPC cells with CDDP, MX and another antimetabolic anticarcinoma agent, Fluorouracil (5-FU), respectively with or without the existence of 3 g/mL MXF. The results of MTT assay indicated that the sensitivity of CNE2 and HONE1 cells to 5-FU, CDDP and MX were enhanced by MXF. The sensitivity of CNE1 cells to CDDP and MX, and the sensitivity of SUNE1 cells to 5-FU and MX were improved by MXF as well (FIG. 6).

The present inventors surprisingly found that *mycoplasma* infection gives rise to a MDR of human cancer cells. *Mycoplasma*-eradication or blockage of interaction between *mycoplasma* and host cell inhibits this *mycoplasma*-induced MDR. It is anticipated that any agent which interrupts the signaling pathways in cancer cells triggered by *mycoplasma* infection is potential to bring down the *mycoplasma*-induced MDR as well. Anti-*mycoplasma* strategy can be tried in combined chemotherapy against cancer by suppressing *mycoplasma*-induced MDR.

It should be understood that although the present invention has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure.

The materials, methods, and examples provided here are representative of preferred embodiments, are exemplary, and are not intended as limitations on the scope of the disclosure.

The disclosure has been described broadly and generically herein. Each of the narrower species and sub-generic groupings falling within the generic disclosure also form part of the disclosure. This includes the generic description of the disclosure with a proviso or negative limitation removing any subject matter from the genus, regardless of whether or not the excised material is specifically recited herein. In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control. The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

The invention claimed is:

1. A method for treatment of a mycoplasma-induced multi-drug resistant tumor in a subject,
   wherein the mycoplasma-induced multi-drug resistant tumor is resistant to at least two classes of chemotherapeutic agents selected from an alkylating agent, an antibiotic, an antimetabolite, an immunotherapy, a hormone or hormone antagonist, a taxane, a retinoid, an alkaloid, an antiangiogenic agent, a topoisomerase inhibitor, a kinase inhibitor, a targeted signal transduction inhibitor, and a biological response modifier,
   the method comprising administering to the subject in need of treatment a therapeutically effective amount of a between membrane protein P37 inhibitor, prior to, at the same time with, or after chemotherapy.

2. The method of claim 1, wherein the P37 inhibitor is selected from an antisense oligomer selected from dsRNA, siRNA, and shRNA directed against P37 protein; and an P37 antibody or a fragment thereof.

3. The method of claim 2, wherein the P37 antibody is a polypeptide A2PP.

4. The method of claim 1, wherein the chemotherapy is carried out by administering one or more chemotherapeutic agents selected from an alkylating agent, an antibiotic, an antimetabolite, an immunotherapy, a hormone or hormone antagonist, a taxane, a retinoid, an alkaloid, an antiangiogenic agent, a topoisomerase inhibitor, a kinase inhibitor, a targeted signal transduction inhibitor, and a biological response modifier.

5. The method of claim 1, wherein the administration is performed prior to chemotherapy.

\* \* \* \* \*